US010221296B2

(12) United States Patent
Steensma et al.

(10) Patent No.: US 10,221,296 B2
(45) Date of Patent: Mar. 5, 2019

(54) POWDER MIXTURE COMPRISING ORGANIC PEROXIDE

(71) Applicant: Akzo Nobel Chemicals International B.V., Arnhem (NL)

(72) Inventors: Maria Steensma, Arnhem (NL); Markus Oliver Majoor, Amersfoort (NL); Martin Hermanus Maria Jensen, Wijhe (NL); Albert Roland Zuijderduin, Joure (NL); Antonie Den Braber, Arnhem (NL)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 58 days.

(21) Appl. No.: 15/536,241

(22) PCT Filed: Dec. 15, 2015

(86) PCT No.: PCT/EP2015/079680
§ 371 (c)(1),
(2) Date: Jun. 15, 2017

(87) PCT Pub. No.: WO2016/096779
PCT Pub. Date: Jun. 23, 2016

(65) Prior Publication Data
US 2018/0022892 A1    Jan. 25, 2018

(30) Foreign Application Priority Data
Dec. 17, 2014 (EP) .................................... 14198583

(51) Int. Cl.
| C08K 3/30 | (2006.01) |
| C08K 5/14 | (2006.01) |
| C08K 3/013 | (2018.01) |
| C09D 7/40 | (2018.01) |
| C09D 5/03 | (2006.01) |
| C08J 5/12 | (2006.01) |
| C08J 3/22 | (2006.01) |
| C08F 2/44 | (2006.01) |
| C07C 409/34 | (2006.01) |

(52) U.S. Cl.
CPC .............. *C08K 5/14* (2013.01); *C07C 409/34* (2013.01); *C08F 2/44* (2013.01); *C08J 3/223* (2013.01); *C08J 5/121* (2013.01); *C08K 3/013* (2018.01); *C08K 3/30* (2013.01); *C09D 5/03* (2013.01); *C09D 7/40* (2018.01); *C08K 2003/3045* (2013.01)

(58) Field of Classification Search
CPC .. C08K 5/14; C08K 3/013; C08K 2003/3045; C09D 7/40; C09D 5/03
See application file for complete search history.

(56) References Cited

U.S. PATENT DOCUMENTS

| 1,631,903 | A | | 6/1927 | Van Der Lande |
| 2,272,576 | A | | 2/1942 | Penn |
| 3,160,598 | A | | 12/1964 | Delfosse |
| 4,387,044 | A | | 6/1983 | Sanchez et al. |
| 4,402,853 | A | | 9/1983 | Brocklehurst et al. |
| 4,456,711 | A | * | 6/1984 | Pietsch ................ A61L 27/446 523/205 |
| 4,500,658 | A | * | 2/1985 | Fox ...................... A61K 6/083 523/117 |
| 4,829,125 | A | | 5/1989 | Yeo et al. |
| 5,370,818 | A | | 12/1994 | Schleifstein |
| 2002/0156483 | A1 | * | 10/2002 | Voellmicke ........ A61B 17/8822 606/93 |
| 2004/0157954 | A1 | * | 8/2004 | Imai ...................... A61L 24/06 523/115 |
| 2007/0032567 | A1 | * | 2/2007 | Beyar ................... A61L 24/043 523/116 |
| 2007/0082152 | A1 | | 4/2007 | Kodama |
| 2010/0030220 | A1 | * | 2/2010 | Truckai .............. A61B 17/8816 606/93 |
| 2012/0202082 | A1 | * | 8/2012 | Fujii ...................... B05D 7/532 428/474.4 |
| 2013/0022656 | A1 | * | 1/2013 | Eng ..................... A61K 8/0237 424/401 |
| 2015/0038637 | A1 | * | 2/2015 | Tong ................... C08L 23/0815 524/528 |

FOREIGN PATENT DOCUMENTS

| CH | 363329 A | 7/1962 |
| CN | 101418180 A | 4/2009 |
| EP | 0 179 223 A1 | 4/1986 |
| EP | 1 136 473 A1 | 9/2001 |
| JP | H10-101808 A | 4/1998 |
| JP | 2004-515357 A | 5/2004 |
| WO | 97/32845 A1 | 9/1997 |
| WO | 98/54249 A1 | 12/1998 |

(Continued)

OTHER PUBLICATIONS

European Search Report issued in counterpart EP Application No. 14198583.8 dated Jun. 1, 2015.
International Search Report and Written Opinion for PCT/EP2015/079680 dated Mar. 9, 2016.
Database WPI 1-15, Week 197239, Thomson Scientific, London, GB; An 1972-62628T; XP002739604.

*Primary Examiner* — Pegah Parvini
(74) *Attorney, Agent, or Firm* — Matthew D. Kellam

(57) ABSTRACT

Powder mixture comprising: ~20-90 wt % of one or more powdered organic peroxides and ~10-80 wt % of one or more powdered filler materials, at least 60 wt % thereof being barium sulphate.

15 Claims, No Drawings

(56) References Cited

FOREIGN PATENT DOCUMENTS

| WO | 02/048251 A1 | 6/2002 |
| WO | 2010/052294 A1 | 5/2010 |
| WO | 2011/019688 A1 | 2/2011 |
| WO | 2011/138432 A1 | 11/2011 |
| WO | 2013/187949 A1 | 12/2013 |

\* cited by examiner

POWDER MIXTURE COMPRISING ORGANIC PEROXIDE

This application is a national stage filing under 35 U.S.C. § 371 of PCT/EP2015/079680, filed Dec. 15, 2015, which claims priority to European Patent Application No. 14198583.8, filed Dec. 17, 2014, the contents of each of which are each incorporated herein by reference in their entirety.

The present invention relates to a powder mixture comprising an organic peroxide. The invention also relates to a process for the preparation of such a mixture and its use in various applications, including coating compositions.

Organic peroxides are widely used in various applications, such as the initiation of polymerization reactions (for instance polymerization of (meth)acrylates, styrene, and vinyl chloride), the crosslinking of rubbers and elastomers, and the curing of (meth)acrylic resins, unsaturated polyester resins, and vinyl ester resins.

Organic peroxides are rather unstable compounds in the sense that they are prone to decomposition. It is this instability that makes them suitable for the initiation of radical polymerization and curing reactions. But this instability can also lead to safety hazards. Many organic peroxides need to be diluted in order to be allowed to be stored and transported in a safe manner.

This dilution, also called phlegmatization, can be done with a liquid phlegmatizer—resulting in a solution, paste, emulsion, or suspension of the peroxide in said phlegmatizer—or with a solid phlegmatizer. If the organic peroxide itself is in solid form, dilution with a solid phlegmatizer will give a solid mixture of organic peroxide and solid phlegmatizer.

It is of course important that the phlegmatized organic peroxide is stable for a sufficiently long period, meaning that both components remain in homogeneous admixture and do not segregate to form separate phases.

A known solid phlegmatizer for solid organic peroxides is calcium carbonate. An advantage of calcium carbonate is that it is relatively cheap and easy to handle; disadvantages are its hygroscopy and acid sensitivity.

Its hygroscopic properties make this material less suitable as a phlegmatizer for organic peroxides to be used in coating compositions, because it will make such coating compositions very sensitive to water, humid environment, and stains. This problem also exists with other hygroscopic materials, such as magnesium sulphate.

Also it's acid sensitivity makes $CaCO_3$ less suitable in coating applications, more in particular for coatings that may come into contact with acids or that contain acidic ingredients. For instance, contact between $CaCO_3$-containing coatings and acid leads to a reaction which will deteriorate the coating and lead to the evolution of $CO_2$ from the coating. This is evidently undesired and makes $CaCO_3$-containing peroxide compositions unsuitable for use in coatings that may come into contact with acids. It also limits the choice of the other ingredients of the coating composition: they should be non-acidic.

The same problems will also be encountered with peroxide formulations containing other carbonate salts, such as magnesium carbonate or barium carbonate.

It has now been found that phlegmatized organic peroxide powders that are stable to segregation and better suited for coating applications can be prepared by using barium sulphate as phlegmatizer.

$BaSO_4$ is neither hygroscopic, nor acid sensitive, and the small primary particles of this material are transparent and therefore ideal for application in coating compositions and transparent composite systems.

Furthermore, contrary to expectations, it was found possible to prepare a stable powder mixture from two powders that significantly differ in size and density. A stable powder mixture is a mixture that does not segregate in an accelerated segregation test as described in the examples below.

The primary particles of $BaSO_4$ are much smaller than organic peroxide particles. $BaSO_4$ additionally has a much higher density (4.5 g/ml) than solid organic peroxides (1.0-1.3 g/ml). One would therefore expect a mixture of these powders to be unstable. Surprisingly, it is not.

The invention therefore relates to a powder mixture comprising:

20-90 wt % of one or more powdered organic peroxides and 10-80 wt % of one or more powdered filler materials, at least 60 wt % thereof being barium sulphate.

This powder mixture has the form of a powder; in other words: it is not a paste or suspension.

The powder mixture comprises at least 10 wt %, more preferably at least 20 wt %, even more preferably at least 40 wt %, and most preferably at least 50 wt % of the powdered filler material. The powder mixture comprises at most 80 wt %, and most preferably at most 70 wt % of the powdered filler material.

At least 60 wt %, more preferably at least 70 wt %, even more preferably at least 80 wt %, even more preferably at least 90 wt %, and most preferably 100 wt % of the powdered filler material consists of barium sulphate.

Suitable filler materials other than barium sulphate are preferably inorganic filler materials. Examples thereof include carbonates such as calcium carbonate, magnesium carbonate, and barium carbonate, silica, kaolinite, and calcium phosphate.

Organic peroxides that can be present in the powder mixture according to the present invention are organic peroxides that are solid at 20° C. They include dibenzoyl peroxide, substituted dibenzoyl peroxides, di(tert-butylperoxyisopropyl)benzene, dicumyl peroxide, di(dichlorobenzoyl)peroxides, diisopropyl peroxydicarbonate, di(t-butylcyclohexyl)peroxydicarbonate, dicetyl peroxydicarbonate, dimyristyl peroxydicarbonate, and didecanoyl peroxide.

More preferred organic peroxides are dibenzoyl peroxide and substituted dibenzoyl peroxides. Substituted dibenzoyl peroxides have the formula:

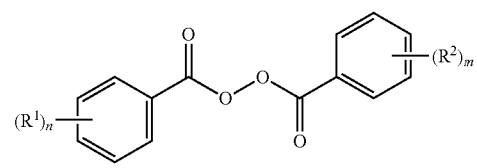

wherein $R^1$ is selected from halogen (Cl, Br, or F) atoms, and linear or branched alkyl, aryl, or aralkyl groups with 1-10 carbon atoms, optionally substituted with O, P, S, and/or Si-containing functionalities, $R^2$ is selected from halogen (Cl, Br, or F) atoms, and linear or branched alkyl, aryl, or aralkyl groups with 1-10 carbon atoms, optionally substituted with O, P, S, and/or Si-containing functionalities, n and m are individually selected from integers in the range 0-5,
and n+m is at least 1.

In a more preferred embodiment, n=m=1.

In a further preferred embodiment, $R^1$ and $R^2$ are both alkyl groups with 1-6 carbon atoms. Even more preferably, $R^1$ and $R^2$ are both methyl groups.

Most preferably, the organic peroxide is benzoyl peroxide or di(4-methylbenzoyl) peroxide. Di(4-methylbenzoyl) peroxide is the most preferred organic peroxide.

The powder mixture comprises at least 20 wt % and most preferably at least 30 wt % of the powdered organic peroxide. The powder mixture comprises at most 90 wt %, more preferably at most 80 wt % even more preferably at most 60 wt %, and most preferably at most 40 wt % of the powdered organic peroxide.

The powder mixture according to the present invention preferably comprises 1-30 wt %, more preferably 1-20 wt %, and most preferably 5-15 wt % of water. The water serves to further increase the safety of the mixture by absorbing the energy that is liberated upon decomposition of the peroxide. The presence of water therefore allows for a better transport classification of the powder mixture.

Barium sulphate preferably contains primary particles with an average particle diameter (d50) of at least 0.1 micron, more preferably at least 0.5 micron. The average primary particle diameter (d50) is preferably below 20 microns, even more preferably below 10 microns, more preferably below 5 microns, and most preferably below 3 microns.

The term "average primary particle diameter" refers to the volume median (d50). It can be determined with laser light diffraction (a HELOS laser light diffraction analyser manufactured by SYMPATEC GmbH and equipped with QUIXEL wet dispersion module) using an ultrasonically pre-treated aqueous suspension comprising 20 wt % of a surfactant (Teepol CH30) and the particles to be measured in an optical concentration between 5 and 25 wt %.

The powder mixture according to the present invention can be prepared by homogenizing and de-agglomerating a mixture of the two powders. The powders are milled until an average primary particle diameter (d50) is reached below 200 microns, as determined with laser light diffraction as described above.

Various devices can be used to homogenize and de-agglomerate the mixture, such as a hammer mill, turbo mill, or pin mill.

If water is present in the mixture, some of it may be removed during or after milling by evaporation (e.g. by mild heating), until the desired water content is obtained.

In a preferred method, water is added to the mixture in the form of a water-containing powdered organic peroxide.

In an even more preferred method, powdered (substituted) dibenzoyl peroxide containing 5-70 wt %, more preferably 10-50 wt %, and most preferably 20-40 wt % of water is milled in the presence of the inorganic filler.

It has surprisingly been found that it is possible to prepare a stable powder mixture from two powders, which differ largely in density. At room temperature, the density of barium sulphate is 4.5 g/ml, whereas the density of solid organic peroxides is in the range 1.0-1.3 g/ml.

The powder mixture according to the present invention finds application as curing agent in coating compositions, in polyester resins and other radically curable thermosetting resins, and as initiator in a radical polymerization processes, such as the polymerization of (meth)acrylic resins.

EXAMPLES

Example 1

Three different compositions of di(4-methylbenzoyl)peroxide and barium sulphate were prepared by manually mixing barium sulphate with di(4-methylbenzoyl)peroxide. The resulting mixtures were treated with a hammer mill equipped with a 1.5 mm sieve to obtain a homogeneous mixture.

The compositions differed in peroxide content and type of barium sulphate (natural or synthetic).

Composition A: 65 wt % synthetic $BaSO_4$ (Blanc Fixe micro, ex. Sachtleben Chemie GmbH; d50=0.7 microns) and 35 wt % di(4-methylbenzoyl)peroxide.

Composition B: 60 wt % natural $BaSO_4$ (CIMBAR EX, ex CIMBAR Performance Minerals; d50=0.8-1.4 microns) and 40 wt % di(4-methylbenzoyl)peroxide containing 25 wt % of water.

Composition C: 60 wt % natural $BaSO_4$ (CIMBAR UF, ex CIMBAR Performance Minerals; d50=1.6-5.8 microns) and 40 wt % di(4-methylbenzoyl)peroxide containing 25 wt % of water Each composition was tested for segregation stability by charging it into a stainless steel cylinder (diameter 10-11 cm, length 50 cm) tilted at an angle of 15° and slowly (7±1 $min^{-1}$) rotating it around its axis for 20±0.5 minutes.

From the upper, middle, and lower part of the cylinder, a sample was taken and the active oxygen content of each sample was determined by iodometric titration. These active oxygen contents were compared with the active oxygen content of the composition prior to the segregation test ('the starting sample').

A mixture is considered to segregate if:

$$(|p_o-p_u|)/p_o>M \text{ or } (|p_o-p_m|)/p_o>M \text{ or } (|p_o-p_l|)/p_o>M$$

wherein: $p_o$=active oxygen content of the starting sample
$p_u$=active oxygen content of the upper layer sample
$p_m$=active oxygen content of the middle layer sample
$p_l$=active oxygen content of the lower layer sample
M=the accepted relative deviation (10%)

The results for the three compositions were as follows:

| | Relative deviation (%) | | |
|---|---|---|---|
| Composition | Upper layer | Middle layer | Lower layer |
| A | 2.4 | 2.4 | 0.7 |
| B | 0.9 | 3.0 | 2.9 |
| C | 2.2 | 1.4 | 0.7 |

All three samples were therefore considered stable to segregation.

Example 2

Two different compositions of a peroxide and barium sulphate were prepared by manually mixing barium sulphate with the peroxide. The resulting mixtures were treated with a hammer mill equipped with a 1.5 mm sieve to obtain a homogeneous mixture.

Composition D: 70 wt % synthetic $BaSO_4$ (Blanc Fixe micro, ex. Sachtleben Chemie GmbH; d50=0.7 microns) and 30 wt % di(tert-butylperoxy-isopropyl)benzene.

Composition E: 70 wt % natural BaSO$_4$ (Blanc Fixe micro, ex. Sachtleben Chemie GmbH; d50=0.7 microns) and 30 wt % dicumylperoxide.

Each composition was tested for segregation stability using the test described in Example 1. The results were as follows:

| Composition | Relative deviation (%) | |
| --- | --- | --- |
| | Upper layer | Lower layer |
| D | 2.9 | 0.6 |
| E | 3.3 | 1.7 |

Both samples were considered stable to segregation.

Comparative Example

A composition comprising 30 wt % di(4-methylbenzoyl) peroxide and 70 wt % magnesium sulphate heptahydrate (ex-Sigma Aldrich) was prepared by manually mixing the magnesium sulphate with di(4-methylbenzoyl)peroxide. Immediately after this mixing, a very wet mixture was obtained that could not be milled. This was due to the hygroscopy of magnesium sulphate.

A powder mixture could therefore not be obtained.

Using anhydrous magnesium sulphate was not an option. Anhydrous magnesium sulphate is very hydroscopic and reacts exothermically with water or moisture. As a result, contact with water or moisture will increase the temperature of the composition and may lead to decomposition of the di(4-methylbenzoyl)peroxide.

The invention claimed is:

1. Powder mixture comprising:
   20-90 wt % of one or more powdered organic peroxides and
   10-80 wt % of one or more powdered filler materials, at least 60 wt % thereof being barium sulphate.

2. Powder mixture according to claim 1 wherein the powder mixture comprises 1-30 wt % of water.

3. Powder mixture according to claim 1 wherein the organic peroxide is selected from the group consisting of dibenzoyl peroxide, substituted dibenzoyl peroxides, di (tert-butylperoxyisopropyl)benzene, dicumyl peroxide, di(dichlorobenzoyl)peroxides, diisopropyl peroxydicarbonate, di(t-butylcyclohexyl)peroxydicarbonate, dicetyl peroxydicarbonate, dimyristyl peroxydicarbonate, and didecanoyl peroxide.

4. Powder mixture according to claim 3 wherein the organic peroxide is selected from the group consisting of dibenzoyl peroxide and substituted dibenzoyl peroxides.

5. Powder mixture according to claim 4 wherein the organic peroxide is di(4-methylbenzoyl) peroxide.

6. Powder mixture according to claim 1 wherein barium sulphate contains primary particles with an average particle size (d50) in the range 0.5-3 microns.

7. Process for the preparation of a powder mixture according to claim 1 wherein 20-90 wt % of one or more powdered organic peroxides and 10-80 wt % of one or more powdered filler materials, at least 60 wt % thereof being barium sulphate, are homogenized and de-agglomerated until an average particle diameter (d50) below 200 microns is reached.

8. Process according to claim 7 wherein the powdered organic peroxide contains 5-70 wt % of water.

9. Process according to claim 7 wherein the organic peroxide is selected from the group consisting of dibenzoyl peroxide, substituted dibenzoyl peroxides, di(tert-butylperoxyisopropyl)benzene, dicumyl peroxide, di(dichlorobenzoyl)peroxides, diisopropyl peroxydicarbonate, di (t-butylcyclohexyl)peroxydicarbonate, dicetyl peroxydicarbonate, dimyristyl peroxydicarbonate, and didecanoyl peroxide.

10. Process according to claim 9 wherein the organic peroxide is selected from the group consisting of dibenzoyl peroxide and substituted dibenzoyl peroxides.

11. Process according to claim 10 wherein the organic peroxide is di(4-methylbenzoyl) peroxide.

12. Coating composition comprising the powder mixture according to claim 1.

13. A method of curing a radically curable thermosetting resin comprising the step of curing the radically curable thermosetting resin with the powder mixture of claim 1.

14. A method of curing a coating composition comprising the step of curing the coating composition with the powder mixture of claim 1.

15. A method for radical polymerization comprising the step of initiating the radical polymerization with the powder mixture of claim 1.

* * * * *